United States Patent [19]

Ashwood

[11] Patent Number: 4,629,734
[45] Date of Patent: * Dec. 16, 1986

[54] BENZOPYRANS
[75] Inventor: Valerie A. Ashwood, Essex, England
[73] Assignee: Beecham Group p.l.c., England
[*] Notice: The portion of the term of this patent subsequent to Nov. 6, 2001 has been disclaimed.
[21] Appl. No.: 610,624
[22] Filed: May 16, 1984
[30] Foreign Application Priority Data May 18, 1983 [GB] United Kingdom ............... 8313679

[51] Int. Cl.$^4$ .................. A61K 31/35; C07D 311/68; C07D 311/70
[52] U.S. Cl. .................. 514/456; 549/399; 549/345; 548/525; 548/407; 548/196; 546/15; 514/422; 514/409; 514/337; 514/278
[58] Field of Search ............... 549/399, 404, 345, 399; 424/283; 546/15, 196; 548/407, 525; 514/456

[56] References Cited

U.S. PATENT DOCUMENTS

| | | | |
|---|---|---|---|
| 4,363,811 | 12/1982 | Evans et al. | 548/525 |
| 4,366,163 | 12/1982 | Evans et al. | 546/196 |
| 4,446,113 | 5/1984 | Evans et al. | 424/267 |
| 4,481,214 | 6/1984 | Evans | 424/283 |

FOREIGN PATENT DOCUMENTS 0046652 3/1982 European Pat. Off. .
0095316 11/1983 European Pat. Off. .
2702092 7/1977 Fed. Rep. of Germany .

OTHER PUBLICATIONS

Lap et al., Aust. J. Chem., 1979, 32, pp. 619–636.

Primary Examiner—Nicky Chan
Attorney, Agent, or Firm—Jacobs & Jacobs

[57] ABSTRACT

Compounds of formula (I):

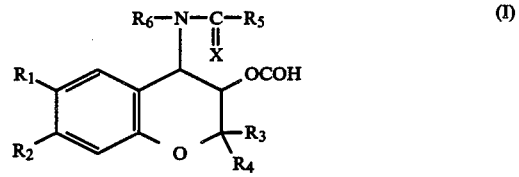

wherein:
$R_1$–$R_6$ are as defined in the specification;
X is oxygen or sulphur; and the $R_6NCXR_5$ and OCOH moieties are trans and, when one or the other of $R_1$ and $R_2$ is an amino group, pharmaceutically acceptable salts thereof, a process and intermediates for preparing them, pharmaceutical compositions containing them, and their use in the treatment of mammals.

9 Claims, No Drawings

BENZOPYRANS

The present invention relates to novel compounds having pharmacological activity, to a process and intermediates for preparing them, to pharmaceutical compositions containing them, and to their use in the treatment of mammals.

U.S. Pat. No. 4,110,347, U.S. Pat. No. 4,251,537, European Patent Publication No. 9912, European Patent Publication No. 28064 and European Patent Publication No. 76075 describe classes of chromans that have blood pressure lowering activity.

A class of chroman derivatives have now been discovered which are characterised by 3-formyl substitution. These have been found to have blood pressure lowering activity.

Accordingly, the present invention provides a compound of formula (I):

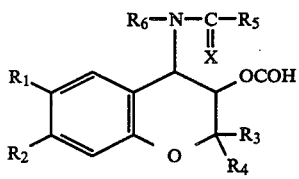

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by a $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
$R_6$ is hydrogen or $C_{1-6}$ alkyl and $R_5$ is hydrogen, $C_{1-6}$ alkyl optionally substituted by hydroxy, $C_{1-6}$ alkoxy, $C_{1-6}$ alkoxycarbonyl or carboxy, $C_{1-2}$ alkyl substituted by halogen, or $C_{2-6}$ alkenyl; or $R_6$ and $R_5$ together form $C_{3-4}$ polymethylene;
X is oxygen or sulphur; and
the $R_6NCXR_5$ and OCOH moieties are trans, or, when one or the other of $R_1$ and $R_2$ is an amino group, a pharmaceutically acceptable salt thereof.

When one of $R_1$ and $R_2$ is hydrogen, the other is favourably selected from the class of $C_{1-6}$ alkylcarbonyl, $C_{1-6}$ alkoxycarbonyl, nitro and cyano. In particular, when one of $R_1$ and $R_2$ is hydrogen, the other is preferably nitro or cyano, or $C_{1-6}$ alkylcarbonyl such as acetyl.

When one of $R_1$ and $R_2$ is hydrogen, it is preferred that $R_2$ is hydrogen.

When one of $R_1$ and $R_2$ is nitro, cyano or $C_{1-3}$ alkylcarbonyl and the other is not hydrogen, the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alky-containing groups for $R_1$ or $R_2$ are, preferably, methyl or ethyl.

Favourably, $R_3$ and $R_4$ are each alkyl having from 1 to 4 carbon atoms. In particular, they are both methyl or ethyl, preferably both methyl.

Suitable values for $R_6$, when $R_5$ and $R_6$ together are not $C_{3-4}$ polymethylene, include hydrogen, methyl, ethyl, n- and iso-propyl, n-, sec- and tert-butyl. Favourably, $R_6$ is hydrogen or methyl, most preferably hydrogen.

Suitable values for $R_5$, when $R_5$ and $R_6$ together are not $C_{3-4}$ polymethylene, include hydrogen, methyl, ethyl, n- and iso-propyl, n-, sec- and tert-butyl, methyl or ethyl substituted by hydroxy, methoxy, carboxy or chloro, vinyl prop-1-enyl, prop-2-enyl, 1-methylvinyl, but-1-enyl, but-2-enyl, but-3-enyl, 1-methylenepropyl, 1-methylprop-1-enyl and 1-methylpropyl, in their E and Z forms where stereoisomerism exists. Favourably $R_5$ is methyl, ethyl, n- or iso-propyl or vinyl, or in particular, methyl substituted by hydroxy or methoxy.

X is preferably oxygen.

There is a group of compounds within formula (I) of formula (II):

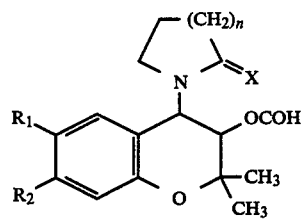

wherein n is 1 or 2 and the remaining variables are as defined in formula (I), the lactam or thiolactam and formyloxy groups being mutually trans.

Suitable and preferred values for the variables are as so described under formula (I).

It will be appreciated that there is a favourable group of compounds within formula (I) of formula (III):

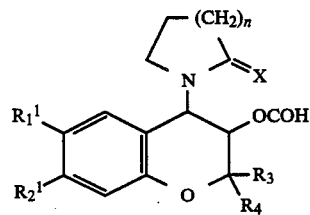

wherein one of $R_1^1$ and $R_2^1$ is hydrogen and the other is cyano, nitro or acetyl, and the remaining variables are as defined in formula (I), the lactam or thiolactam and formyl groups being mutually trans.

Suitable and preferred values for the variables are as so described under formula (I).

From the aforesaid it will be appreciated that there is a preferred compound within formula (III) of formula (IV):

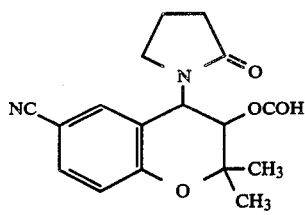

(IV)

wherein the lactam and formyloxy groups are trans to each other.

There is a further group of compounds within formula (I) of formula (V):

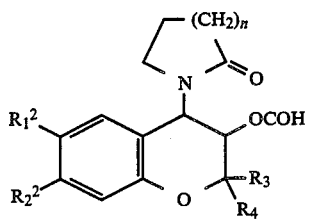

(V)

wherein:
one of $R_1^2$ and $R_2^2$ is cyano or nitro and the other is amino optionally substituted as defined and the remaining variables are as defined in formula (I).

Favourably $R_1^2$ is cyano or nitro and $R_2^2$ is amino. Suitable and preferred values for the remaining variables are as so described under formula (I).

There is a further group of compounds within formula (I) of formula (VI):

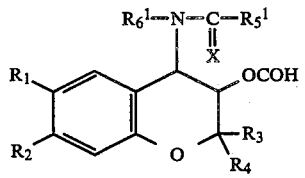

(VI)

wherein $R_6^1$ is hydrogen or $C_{1-6}$ alkyl and $R_5^1$ is hydrogen or $C_{1-6}$ alkyl and the remaining variables are as defined in formula (I).

Suitable and preferred values of the variables are as so described for the corresponding variables in formula (I).

There is a favourable sub-group of compounds within formula (VI) of formula (VII):

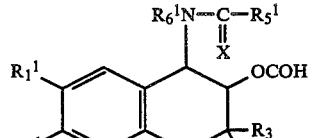

(VII)

Suitable and preferred values for the variables are as so described for the corresponding variables under formula (I).

A preferred sub-group of compounds within formula (VII) is of formula (VIII):

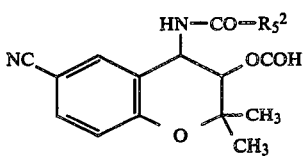

(VIII)

wherein $R_5^2$ is hydrogen or $C_{1-4}$ alkyl, preferably hydrogen or methyl, in particular hydrogen.

The compounds of the formula (I) have asymmetric centres and, therefore, can exist as enantiomers. The present invention extends to all such isomers individually and as mixtures, such as raceates.

The present invention also provides a process for the preparation of a compound of formula (I) or a pharmaceutically acceptable salt thereof, which process comprises the reaction of a compound of formula (IX):

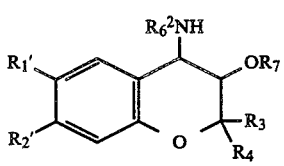

(IX)

wherein
the $R_6^2NH$ and $OR_7$ moieties are trans;
$R_1'$ and $R_2'$ are $R_1$ and $R_2$ respectively as hereinbefore defined or a group atom convertible thereto;
$R_7$ is hydrogen, $C_{1-6}$ alkyl or $C_{1-8}$ acyl; and
$R_6^2$ is hydrogen or $C_{1-6}$ alkyl;:
with a compound of formula $R_8COQ_1$ wherein
$R_8$ is hydrogen, optionally substituted $C_{1-6}$ alkyl as hereinbefore defined for $R_5$, $C_{1-2}$ alkyl substituted by halogen, $C_{2-6}$ alkenyl or (when $R_6^2$ is hydrogen), $Q_2(CH_2)_{n+2}$ where $Q_2$ is a leaving group and n is 1 or 2; and
$Q_1$ is a leaving group;
and thereafter converting $R_1'$ or $R_2'$ when a group or atom convertible to $R_1$ and $R_2$ to $R_1$ or $R_2$ as hereinbefore defined; optionally converting $R_1$ or $R_2$ to other $R_1$ or $R_2$; cyclising the compound formed when $R_8$ is $Q_2(CH_2)_{n+2}$ as hereinbefore defined; as necessary converting $R_7$ as hereinbefore defined in the resultant compound to formyl; optionally thiating a resulting compound wherein X is oxygen; and when one of $R_1$ and $R_2$ in the compound of formula (I) is an amino group, optionally forming a pharmaceutically acceptable salt thereof.

The leaving group $Q_1$ is a group that is displaceable by a primary or secondary amino nucleophile. Examples of such a group include hydroxy, and, when $R_8$ is other than hydrogen, $C_{1-4}$ alkoxy, $C_{1-4}$ alkylcarbonyloxy, and halogen, such as chloro and bromo. When the leaving group $Q_1$ is any of these examples, the acylating agent is an acid, an ester, an acid anhydride or When the acylating agent is an acid, the reaction may be carried out in the presence of a dehydrating agent, such as dicyclohexylcarbodiimide. When the acid is formic acid this is not generally necessary; a base When the acylating agent is an acid anhydride, the acylation of the compound of formula (IX) is, preferably, carried out using the anhydride as the solvent in the presence of an acid acceptor, such as sodium acetate.

When the acylating agent is an acid halide, the acylation of the compound of formula (IX) is, preferably, carried out in an aqueous medium, such as chloroform/water, in the presence of an acid acceptor, such as triethylamine, trimethylamine, pyridine, picoline or calcium, potassium or sodium carbonate.

Conversions of a group or atom $R_1'$ or $R_2'$ into $R_1$ or $R_2$ as defined hereinbefore are generally known. For example, it is preferred, when carrying out the reaction, to protect any unsubstituted amino moieties, such as when the $R_1/R_2$ is amino, with a protecting agent. Examples of protecting agents include acyl groups, such as acetyl. Removal of the acyl protecting agent is carried out by base hydrolysis.

If it is desired to protect an amino group in the presence of a cyano group then a more suitable method is to use a trifluoroacetyl protecting group which may be removed by mild hydrolysis. A further suitable method of deprotection of a protected amino group in the presence of a cyano group is to utilise a benzyloxycarbonyl or p-nitrobenzyloxycarbonyl protecting group, which groups may be removed by mild catalytic hydrogenolysis. Benzyloxycarbonyl-amino and p-nitrobenzyloxycarbonylamino groups may be formed by reaction of the appropriate chloride with the free amine function.

As an additional example, a hydrogen atom may be replaced by a nitro group by nitrating in a known manner a compound of formula (I), wherein one of $R_1'$ and $R_2'$ is hydrogen. Also, an acetamido group may be converted to hydrogen, by hydrolysing a compound of formula (I) wherein one of $R_1'$ and $R_2'$ is acetamido, converting the resulting amine into a diazonium salt, and finally decomposing it, leaving a compound of formula (I), wherein one of $R_1$ and $R_2$ is hydrogen.

The protection of a carbonyl-containing $R_1$ or $R_2$ group during the optional thiation step of the process of the present invention is described hereinafter in conjunction with that step.

The known methods of $R_1'$ and $R_2'$ interconversion with $R_1$ and $R_2$ (lying in within the definition of $R_1'$ and $R_2'$) are applicable to any $R_1'$ and $R_2'$ interconversions hereinafter.

It is however preferred that any conversions are carried out at an earlier stage as mentioned hereinafter.

Examples of optional conversions of $R_1$ or $R_2$ in a compound of formula (I) into another $R_1$ or $R_2$, as defined hereinbefore, are generally known in the art of aromatic chemistry. For example, an α-hydroxyethyl group may be converted into acetyl by oxidation, or an amino group may be converted into a chloro atom by the Sandmeyer reaction, an amino group may be converted into amino substituted by one or two $C_{1-6}$ alkyl or by $C_{2-7}$ alkanoyl, or a hydrogen atom may be converted into a nitro group by nitration.

$R_7$ when other than formyl may be converted to formyl by conventional procedures. $R_7$ hydrogen may be converted to formyl by formylation using formic acid or a formyl halide. It is, however, preferred that $R_7$ is other than hydrogen because of the risk of side reactions between the 3-hydroxy group and the compound of formula $R_8COQ_1$ where the variables are as hereinbefore defined, or with a thiating agent in the optional thiation step, in the process of the present invention. Other $R_7$ groups may effectively be used as a hydroxy-protecting function and, if other than formyl, subsequently converted conventionally to formyl to give the desired 3-formyloxy group. For example, it is convenient to use a compound of formula (IX) having a labile $C_{1-8}$ acyl group such as mesyl or tosyl, which may be converted to hydrogen by conventional base hydrolysis and then converted to formyl by conventional formylation or converted directly to formyl by a base-catalysed transesterification reaction.

It will be appreciated, however, that when $R_8$ is hydrogen it may be convenient for $R_7$ to be hydrogen in the compound of formula (IX) in which case the 3-hydroxy group and the group $R_6^2NH$ are formylated simultaneously.

It will also be appreciated that if the preferred Lawesson's reagent is used for the thiation step (see hereinafter), then protection of any $R_7O$ hydroxy group will not be necessary.

Suitable examples for $R_7$ when alkyl include methyl, ethyl, n- and iso-propyl. Suitable examples for $R_7$ when acyl include carboxylic acyl such as acetyl, propionyl and benzoyl.

When $R_8Q_2(CH_2)_{n+2}$ where the variables are as hereinbefore defined, the leaving group $Q_2$ is a group that is displaceable by a secondary amino nucleophile adjacent to a carbonyl function. A preferred example is chloro.

The cyclisation reaction when $R_8$ is $Q_2(CH_2)_{n+2}$ where the variables are as hereinbefore defined is preferably carried out in an inert solvent such as dimethylformamide.

The thiation reaction is preferably carried out with conventional thiation agents, such as hydrogen sulphide, phosporous pentasulphide and Lawesson's reagent (p-methoxyphenylthiophosphine sulphide dimer). The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is carried out at temperatures from room temperatures to reflux in a dry solvent, such as toluene or methylene chloride.

When thiation is to be used to prepare a compound of formula (I) wherein X is sulphur and $R_1$ or $R_2$ is a carbonyl-containing group, then it is preferred to use the corresponding compound of formula (IX), wherein $R_1'$ or $R_2'$ is a protected carbonyl-containing group, in the thiation reaction, and afterwards to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

When one of $R_1$ and $R_2$ in the compound of formula (I) so obtained is an amino or an amino-containing group, the optional formation of a pharmaceutically accetpable salt thereof may be carried out by conventional procedures.

A compound of formula (IX) may be prepared by reacting a compound of formula (X):

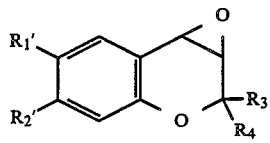   (X)

wherein $R_1'$, $R_2'$, $R_3$ and $R_4$ are as defined hereinbefore, with a compound of formula (XI):

$R_6{}^2NH_2$   (XI)

or a salt thereof, wherein $R_6{}^2$ is as hereinbefore defined,; and optionally converting the $R_7O$ hydroxy group in the resulting compound of formula (IX) into a $C_{1-6}$ alkoxy or $C_{1-8}$ acyloxy group.

The reaction is normally carried out in a solvent, such as a $C_{1-4}$ alcohol, in particular methanol, ethanol or propanol at an ambient or an elevated temperature, for example 10° to 100° C. The reaction proceeds particularly smoothly if carried out in ethanol under reflux.

The resulting compound of formula (IX) may be removed from the reaction mixture by removal of the solvent, for example, by evaporation under reduced pressure. Any epoxide impurity may be removed conventionally, for example by chromatography.

Examples of an optional conversion of $R_7O$ in a compound of formula (IX) into another $R_7O$ are generally known in the art. For example, when $R_7O$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent, such as dicyclohexylcarbodiimide. Alternatively, when $R_7O$ is $C_{1-8}$ acyloxy it may be converted into hydroxy by conventional hydrolysis with for example, dilute mineral acid.

A compound of formula (X) may be prepared, preferably in situ, by reacting a compound of formula (XII):

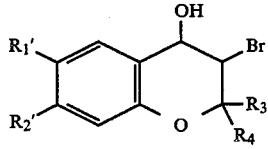   (XII)

wherein $R_1'$, $R_2'$, $R_3$ and $R_4$ are as hereinbefore defined and the hydroxy group is trans to the bromo atom, with a base, such as potassium hydroxide, in a solvent, such as ether or aqueous dioxan.

Compounds of formula (XII) are known and may be prepared in accordance with any appropriate known process, for example, by the process described in the aforementioned U.S. patents and European patent publications. Schematically, such process can be depicted thus.

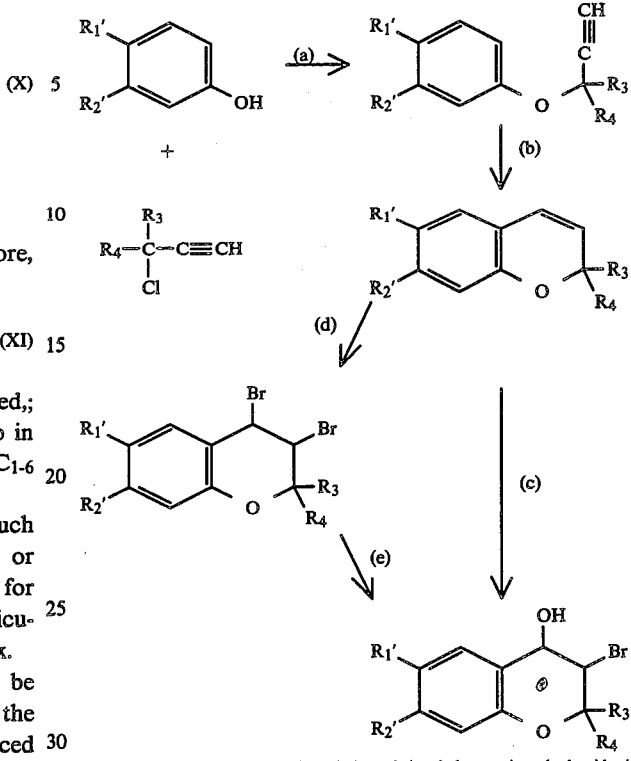

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

Alternatively, a compound of formula (I), or a pharmaceutically acceptable salt thereof, wherein $R_5$ and $R_6$ together are $C_{2-5}$ polymethylene may be prepared by oxidising a compound of formula (XIII) or a metal salt thereof:

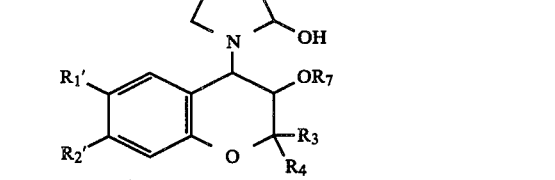   (XIII)

wherein $R_1'$, $R_1'$, $R_3$, $R_4$ and $R_7$ and n are as defined hereinbefore, and wherein the cyclic aminol group is trans to the $OR_7$ group; and converting $R_1'$ or $R_2'$ in the resultant compound to $R_1$ or $R_2$ as hereinbefore defined; optionally converting $R_1$ or $R_2$ in the resultant compound to other $R_1$ and $R_2$ as hereinbefore defined; as necessary converting $R_7$ as hereinbefore defined to formyl; optionally thiating a resulting compound wherein X is oxygen; and where one of $R_1$ and $R_2$ in the compound of formula (I) is amino, optionally forming a pharmaceutically acceptable salt thereof.

The oxidation is preferably carried out in a solvent such as aqueous methanol with a metal periodate such as potassium periodate.

A compound of formula (XII) may be prepared by cyclising in the presence of an acid a compound of formula (XIV):

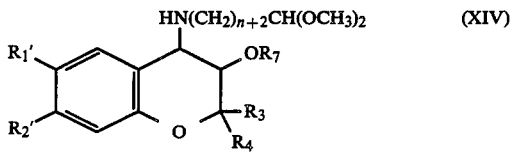

wherein $R_1'$, $R_2'$, $R_3$, $R_4$ and $R_5$ and n are as defined hereinbefore and wherein the substituted amino group is trans to the $OR_7$ group.

A compound of formula (XIV) may in turn be prepared by reacting a compound of formula (X) with a compound of formula (XV):

wherein n is as defined hereinbefore.

Compounds of formulae (IX) or (XIII) wherein $R_7$ is formyl are believed to be novel, and as such form an aspect of the present invention.

As a further alternative, a compound of formula (I), or a pharmaceutically acceptable salt thereof wherein $R_5$ and $R_6$ together are $C_{2-5}$ polymethylene may be prepared by reacting a compound of formula (X) with an anion of formula (XVI):

wherein n is as defined hereinbefore; and optionally converting $R_1'$ or $R_2'$ in the resultant compound to $R_1$ or $R_2$ as hereinbefore defined; optionally converting $R_1$ or $R_2$ in the resultant compound to other $R_1$ or $R_2$ as hereinbefore defined; converting the 3-hydroxy group to formyloxy; optionally thiating a resulting compound wherein X is oxygen; and where one of $R_1$ and $R_2$ in the compound of formula (I) is imino, optionally forming a pharmaceutically acceptable salt thereof.

The reaction is preferably carried out in a solvent such as dimethylsulphoxide in the presence of a base, such as sodium hydride.

A compound of formula (X) may be prepared in situ from the corresponding compound of formula (XII). In such circumstances, it is advantageous not to add the lactam anion of formula (XVI) until sufficient time has elapsed for the epoxide of formula (X) to be produced.

As mentioned previously, the compounds of formula (I) exist in optically active forms, and the processes of the present invention produces mixtures of such forms. The individual isomers may be separated one from the other by chromatography using a chiral phase.

It is preferred that the compounds of formula (I) are isolated in substantially pure form, or in crystalline form.

As mentioned previously, the compounds of formula (I) have been found to have blood-pressure lowering activity. They are therefore useful in the treatment of hypertension.

The present invention accordingly provides a pharmaceutical composition which comprises a compound of formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof and a pharmaceutically acceptable carrier.

The compositions are preferably adapted for oral administration. However, they may be adapted for other mode of administration, for example parenteral administration for patients suffering from heart failure.

The compositions can be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The present invention further provides a compound of formula (I) or a pharmaceutically acceptable salt thereof for use in the treatment or prophylaxis of hypertension.

The following descriptions relate to the preparation of intermediates and the following examples relate to the preparation of a compound of formula (I).

All temperatures therein are in °C.

DESCRIPTION 1

6-Cyano-3,4-dihydro-2,2-dimethyl-3,4-epoxy-2H-benzo-[b]pyran

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperature for 1.5 hours under nitrogen. After distillation of the solvent the fraction boiling at 110°-1140°/0.02 mmHg (16.57 g) was collected, which on standing formed a low melting solid, having an IR absorption at 2230 cm$^{-1}$. (See M. Harfenist and E. Thom, J. Org. Chem., 37, 841 (1972) who quote m.p. 36°-37°).

Addition to this 6-cyanochrome (16.50 g) dissolved in dimethyl sulphoxide (150 ml) containing water (3.24 ml), of N-bromosuccinimide (31.90 g) with vigorous stirring and cooling, followed by dilution with water and extraction via ethyl acetate gave a mixture which was boiled in acetone (300 ml) and water (100 ml) for 5 hours to hydrolyse the small amount of 3,4-dibromide present. Evaporation of solvents gave 6-Cyano-trans-3-bromo-3,4-dihydro-2,2-dimethyl-2H-benzo[b]pyran-4-ol as white crystals (24.37 g). A small sample had m.p. 128°-128.5° from 60°-80° petroleum ether, nmr (CDCl$_3$).

1.43 (3H), 1.62 (3H), 7.48 (1H, exchangeable) 4.07 (1H, d, J=9), 4.87 (1H, d, J=9), 6.80 (1H, d, J=8), 7.43 (1H, q, J=8 2), 7.78 (1H, d, J=2).

Anal. Calcd. for C$_{12}$H$_{12}$NO$_2$Br: C, 51.07; H, 4.26; N, 4.96; Br, 28.37. Found: C, 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 6-cyano-3,4-dihydro-2,2-dimethyl-3,4-epoxy-2H-benzo[b]pyran 16.02 g) as a gum, having an absorption at 2230 cm$^{-1}$ in the IR and Nmr (CCl$_4$) 1.26 (3H, 1.54 (3H), 3.40 and 3.80 (each 1H, d, J=4), 6.77 (1H, d, J=8), 7.43 (1H, q, J=8, 2), 7.58 (1H, d, J=2).

DESCRIPTION 2

6-Cyano-3,4-dihydro-2,2-dimethyl-trans-4-amino-2H-benzo[b]pyran-3-ol

The title compound was prepared by stirring 6-cyano-3,4-dihydro-2,2-dimethyl-3,4-epoxy-2H-benzo[b]pyran in ethanolic ammonium hydroxide solution at room temperature until thin layer chromatography showed consumption of the starting epoxide.

EXAMPLE 1

Trans-6-cyano-4-formylamino-3,4-dihydro-2,2-dimethyl-2H-1-benzopyran-3-yl formate

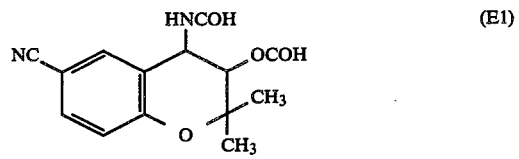
(E1)

Trans-4-amino-6-cyano-3,4-dihydro-2,2-dimethyl-2H-1-benzopyran-3-ol *(0.90 g) was heated under reflux in formic acid (15 ml) and pyridine (1 ml) during 19 hr. The cooled solutions was poured into water and extracted with ethyl acetate. The organic layer was washed with water and dried over anhydrous magnesium sulphate. Filtration and evaporation left an orange coloured oil which was chromatographed (chromatotron, ethyl acetate-pentane gradient elution on 2 mm silica gel, flow rate 9 ml/min) to give after recrystallisation from ethyl acetate-pentane the title compound (0.15 g) as crystals of m.p. 171°-172° C.

*The starting material was prepared in accordance with the procedure described in European Patent Publication No. 76 075.

NMR (CDCl$_3$) δ 1.37 (3H, s); 1.45 (3H, s); 5.20 (1H, d, J=12 Hz); 5.45 (1H, t, J=12, 12 Hz); 5.98 (1H, irreg d, J=12 Hz); 6.90 (1H, d, J=9 Hz); 7.47 (1H, q, J=9, 2 Hz) overlapped by; 7.55 (1H, d, J=2 Hz); 8.20 (1H, s); 8.43 (1H, s).

6-nitro-trans-4-formylamino-3,4-dihydro-2,2-dimethyl-2H-1-benzo[b]pyran-3-yl formate (E3), 6-acetyl-trans-4-formylamino-3,4-dihydro-2,2-dimethyl-2H-1-benzo[b]pyran-3-yl formate (E4),
6-cyano-trans-4-N-formyl-N-methylamino-3,4-dihydro-2,2-dimethyl-2H-1-benzo[b]pyran-3-yl formate (E5),
6-nitro-trans-4-N-formyl-N-methylamino-3,4-dihydro-2,2-dimethyl-2H-1-benzo[b]pyran-3-yl formate (E6),
6-acetyl-trans-4-formyl-N-methylamino-3,4-dihydro-2,2-dimethyl-2H-1-benzo[b]pyran-3-yl formate (E7)
are prepared analogously.

EXAMPLE 2

6-Cyano-3,4-dihydro-2,2-dimethyl-trans-4-(2-oxo-1-yrrolidinyl)-2H-benzo[b]pyran-3-yl formate (E2)

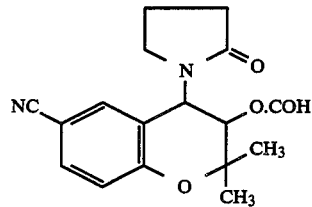

6-Cyano-3,4-dihydro-2,2-dimethyl-trans-4-(2-oxo-1-pyrrolidinyl)-2H-benzo[b]pyran-3-ol (1.0 g) was heated under reflux in formic acid (15 ml) containing pyridine (1 ml) for 18 hours. On cooling the reaction mixture was poured into water (100 ml) and extracted with ethyl acetate (3×50 ml). The organic layer was washed with water, and brine and dried over anhydrous magnesium sulphate. Filtration and evaporation gave a crude product (0.75 g) which was purified by chromatography (chromatotron, ethyl acetate-pentane gradient) and recrystallisation from ethyl acetate-pentane to give the title ester (0.30 g) of m.p. 182°–183° C.

6-nitro-3,4-dihydro-2,2-dimethyl-trans-4-(2-oxo-1-pyrrolidinyl)-2H-benzo b pyran-3-yl formate (E8),
6-acetyl-3,4-dihydro-2,2-dimethyl-trans-4-(2-oxo-1-pyrrolidinyl)-2H-benzo b pyran-3-yl formate (E9),
6-cyano-3,4-dihydro-2,2-dimethyl-trans-4-(2-oxo-1-piperidinyl)-2H-benzo b pyran-3-yl formate (E10),
6-nitro-3,4-dihydro-2,2-dimethyl-trans-4-(2-oxo-1-piperidinyl)-2H-benzo b pyran-3-yl formate (E11) and
6-acetyl-3,4-dihydro-2,2-dimethyl-trans-4-(2-oxo-1-piperidinyl)-2H-benzo b pyran-3-yl formate (E12)
are prepared analogously.

PHARMACOLOGICAL DATA

Systolic blood pressures were recorded by a modification of the tail cuff method described by I M Claxton, M G Palfreyman, R H Poyser, R L Whiting, European Journal of Pharmacology, 37, 179 (1976). A W+W BP recorder, model 8005, was used to display pulses prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| Compound (E1) | Time Post Dose Hours | % Change in Systolic Blood Blood | % Change in Heart Rate |
|---|---|---|---|
| 6 rats | 1* | −37 ± 7 | 8 ± 7 |
| Dose 10 mg/kg p.o. | 2* | −42 ± 8 | 10 ± 6 |

-continued

| Compound (E1) | Time Post Dose Hours | % Change in Systolic Blood Blood | % Change in Heart Rate |
|---|---|---|---|
| Initial Blood Pressure 216 ± 5 mmHg Initial Heart Rate 455 ± 15 beats/min | 4* | −34 ± 6 | 0 ± 2 |
| | 6** | −50 | 1 |

*1 rat had no measurable pulse
**5 rats had no measurable pulse

I claim:
1. A compound of formula (I):

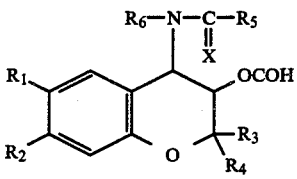

wherein:
either one of $R_1$ and $R_2$ is hydrogen and the other is selected from the class of $C_{1-7}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
$R_6$ is hydrogen or methyl and $R_5$ is hydrogen;
X is oxygen or sulphur; and
the $R_6NCXR_5$ and OCOH moieties are trans, or, when one or the other of $R_1$ and $R_2$ is an amino group, a pharmaceutically acceptable salt thereof.
2. A compound according to claim 1, wherein one of $R_1$ and $R_2$ is hydrogen and the other is selected from the class of $C_{1-6}$ alkylcarbonyl, $C_{1-6}$ alkoxycarbonyl, nitro and cyano.
3. A compound according to claim 1, wherein one of $R_1$ and $R_2$ is hydrogen and the other is nitro, cyano or acetyl.
4. A compound according to claim 1 wherein $R_2$ is hydrogen.
5. A compound according to claim 1 wherein $R_5$ is hydrogen, $R_6$ is hydrogen and X is oxygen.
6. A compound which is
6-cyano-trans-4-formylamino-3,4-dihydro-2,2-dimethyl-2H-1-benzo[b]pyran-3-yl formate, 6-nitro-trans-4-formylamino-3,4-dihydro-2,2-dimethyl-2H-1-benzo[b]pyran-3-yl formate, 6-acetyl-trans-4-formylamino-3,4-dihydro-2,2-dimethyl-2H-1-benzo[b]pyran-3-yl formate, 6-cyano-trans-4-(N-formyl-N-methylamino)-3,4-dihydro-2,2-dimethyl-2H-1-benzo[b]pyran-3-yl formate, 6-nitro-trans-4-(N-formyl-N-methylamino)-3,4-dihydro-2,2-dimethyl-2H-1-benzo[b]pyran-3-yl formate, or 6-acetyl-trans-4-(N-formyl-N-methylamino)-3,4-dihydro-2,2-dimethyl-2H-1-benzo[b]pyran-3-yl formate.

7. A compound according to claim 1 which is 6-cyano-trans-4-formylamino-3,4-dihydro-2,2-dimethyl-2H-1-benzo[b]pyran-3-yl formate.

8. An anti-hypertensive pharmaceutical composition which comprises an anti-hypertensive effective amount of a compound according to claim 1 of formula (I) or a pharmaceutically acceptable salt thereof and a pharmaceutically acceptable carrier.

9. A method of treatment of hypertension in mammals including man, which comprises administering to the suffering mammal an anti-hypertensive effective amount of a compound of formula (I):

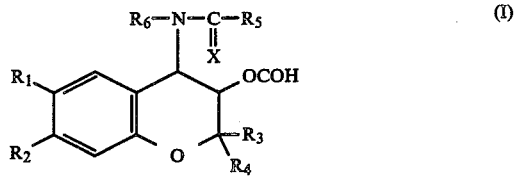

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

$R_6$ is hydrogen or $C_{1-6}$ alkyl and $R_5$ is hydrogen, $C_{1-6}$ alkyl optionally substituted by hydroxy, $C_{1-6}$ alkoxy, $C_{1-6}$ alkoxycarbonyl or carboxy, $C_{1-2}$ alkyl substituted by halogen, or $C_{2-6}$ alkenyl;

X is oxygen or sulphur; and the $R_6NCXR_5$ and OCOH moieties are trans, or, when one or the other of $R_1$ and $R_2$ is an amino group, a pharmaceutically acceptable salt thereof.

* * * * *